(12) United States Patent
Kim et al.

(10) Patent No.: US 9,090,919 B2
(45) Date of Patent: Jul. 28, 2015

(54) METHOD OF PRODUCING 3-HYDROXYPROPIONIC ACID FROM GLYCEROL

(75) Inventors: Chul-Ho Kim, Daejeon (KR); Jeong-Woo Seo, Seoul (KR); Lianhua Luo, Jeollabuk-do (KR); Baek Rock Oh, Gwangju (KR); Pil-Soo Seo, Busan (KR); Sun-Yeon Heo, Jeollabuk-do (KR)

(73) Assignee: KOREA RESEARCH INSTITUTE OF BIOSCIENCE AND BIOTECHNOLOGY (KR)

( * ) Notice: Subject to any disclaimer, the term of this patent is extended or adjusted under 35 U.S.C. 154(b) by 514 days.

(21) Appl. No.: 13/505,111

(22) PCT Filed: Oct. 29, 2009

(86) PCT No.: PCT/KR2009/006278
§ 371 (c)(1),
(2), (4) Date: Jul. 5, 2012

(87) PCT Pub. No.: WO2011/052819
PCT Pub. Date: May 5, 2011

(65) Prior Publication Data
US 2012/0270287 A1    Oct. 25, 2012

(51) Int. Cl.
*C12P 7/18* (2006.01)
*C12P 7/42* (2006.01)
(Continued)

(52) U.S. Cl.
CPC . *C12P 7/42* (2013.01); *C07K 14/26* (2013.01); *C12N 9/0006* (2013.01); *C12N 9/0008* (2013.01); *C12P 7/18* (2013.01); *C12P 7/52* (2013.01)

(58) Field of Classification Search
CPC ............... C12P 7/18; C12P 7/42; C12P 7/52; C12N 9/0006; C12N 9/0008; C07K 14/26
See application file for complete search history.

(56) References Cited

U.S. PATENT DOCUMENTS 5,321,156 A    6/1994 Behr et al.
5,831,121 A    11/1998 Haas et al.
(Continued)

FOREIGN PATENT DOCUMENTS

JP        2000159724 A    6/2000
KR    1020020000030 A    1/2002

OTHER PUBLICATIONS

Den, H., et al., 1959, "Enzymatic conversion of β-hydroxypropionate to malonic semialdehyde", Journal of Biological Chemistry, vol. 234, No. 7, pp. 1666-1671.*

(Continued)

*Primary Examiner* — Manjunath Rao
*Assistant Examiner* — William W Moore
(74) *Attorney, Agent, or Firm* — Tristan A. Fuierer; Moore & Van Allen, PLLC

(57) ABSTRACT

The present invention relates to a novel method of producing 3-hydroxypropionic acid from glycerol, and more particularly to a method of producing 3-hydroxypropionic acid by culturing in a glycerol-containing medium a mutant microorganism obtained by amplifying an aldehyde dehydrogenase-encoding gene in a microorganism having the abilities to produce coenzyme B12 and produce 3-hydroxypropionic acid using glycerol as a carbon source. The present invention enables the fermentation of glycerol even under microaerobic or aerobic conditions without having to add coenzyme B12. Thus, the invention will be very suitable for the development of biological processes for producing large amounts of 3-hydroxypropionic acid.

2 Claims, 8 Drawing Sheets

(51) Int. Cl.
*C12P 7/52* (2006.01)
*C07K 14/26* (2006.01)
*C12N 9/02* (2006.01)
*C12N 9/04* (2006.01)

(56) References Cited

U.S. PATENT DOCUMENTS

| | | | |
|---|---|---|---|
| 6,329,183 B1 * | 12/2001 | Skraly et al. | 435/135 |
| 6,432,686 B1 | 8/2002 | Bulthuis et al. | |
| 6,576,450 B2 * | 6/2003 | Skraly et al. | 435/135 |
| 6,852,517 B1 * | 2/2005 | Cameron et al. | 435/135 |
| 7,524,660 B2 * | 4/2009 | Caimi et al. | 435/159 |
| 7,858,350 B2 * | 12/2010 | Burk et al. | 435/158 |
| 7,947,483 B2 * | 5/2011 | Burgard et al. | 435/252.1 |
| 8,048,624 B1 * | 11/2011 | Lynch | 435/6.18 |
| 8,067,214 B2 * | 11/2011 | Burk et al. | 435/158 |
| 8,114,643 B2 * | 2/2012 | Skraly et al. | 435/135 |
| 8,748,157 B2 * | 6/2014 | Morishige et al. | 435/252.33 |
| 2004/0152174 A1 * | 8/2004 | Cervin et al. | 435/106 |
| 2005/0239179 A1 * | 10/2005 | Skraly et al. | 435/135 |
| 2006/0252136 A1 * | 11/2006 | Caimi et al. | 435/158 |
| 2007/0148749 A1 * | 6/2007 | Yasuda et al. | 435/158 |
| 2009/0047719 A1 * | 2/2009 | Burgard et al. | 435/158 |
| 2009/0075351 A1 * | 3/2009 | Burk et al. | 435/141 |
| 2009/0253192 A1 * | 10/2009 | Emptage et al. | 435/252.31 |
| 2009/0305368 A1 * | 12/2009 | Morishige et al. | 435/146 |
| 2010/0112654 A1 * | 5/2010 | Burk et al. | 435/158 |
| 2011/0244575 A1 * | 10/2011 | Lipscomb et al. | 435/471 |
| 2012/0045808 A1 * | 2/2012 | Kim et al. | 435/158 |

OTHER PUBLICATIONS

Strauss, G., et al., 1993, "Enzymes of a novel autotrophic CO2 fixation pathway in the phototrophic bacterium *Chloroflexus aurantiacus*, the 3-hydroxypropionate cycle", European Journal of Biochemistry, vol. 215, pp. 633-643.*
Menzel, K., et al., 1997, "Enzymatic evidence for an involvement of pyruvate dehydrogenase in the anaerobic glycerol metabolism of *Klebsiella pneumoniae*," Journal of Biotechnology, vol. 56, pp. 135-142.*
Menzel, K., et al., 1998, "Kinetic, dynamic, and pathway studies of glycerol metabolism by *Klebsiella pneumoniae* in anaerobic continuous culture: IV. Enzymes and fluxes of pyruvate metabolism," Biotechnology and Bioengineering, vol. 60, No. 5, pp. 617-626.*
Daniel, R., et al., 1999, Biochemistry of coenzyme B12-dependent glycerol and diol dehydratases and organization of the encoding genes, FEMS Microbiology Reviews, vol. 22, pp. 553-566.*
Toraya, T., et al., 1999, A reactivating factor for coenzyme B12 dependent-diol dehydratase, Journal of Biological Chemistry, vol. 274, No. 6, pp. 3372-3377.*

Herter, S., et al., 2001, "Autotrophic CO2 fixation by *Chloroflexus aurantiacus*: Study of glyoxylate formation and assimilation via the 3-hydroxypropionate cycle", Journal of Bacteriology vol. 183, No. 14, pp. 4305-4316.*
Hugler, M., et al., 2002, "Malonyl-Coenzyme A reductase from *Chloroflexus aurantiacus*, a key enzyme of the 3-hydroxypropionate cycle for autotrophic CO2 fixation," Journal of Bacteriology, vol. 184, No. 9, pp. 2404-2410.*
Gonzalez-Pajuelo, M., et al., 2005, "Metabolic engineering of *Clostridium acetobutylicum* for the industrial production of 1,3-propanediol from glycerol," Metabolic Engineering, vol. 7, pp. 329-336.*
Alber, B., et al., 2006, "Malonyl-coenzyme A reductase in the modified 3-hydroxypropionate cycle for autotrophic carbon fixation in archaeal *Metallosphaera* and *Sulfolobus* spp.," Journal of Bacteriology, vol. 188, No. 24, pp. 8551-8559.*
Klatt, C. G., et al., 2007, "Comparative genomics provides evidence for the 3-hydroxypropionate autotrophic pathway in filamentous anoxygenic phototrophic bacteria and in hot spring microbial mats," Environmental Microbiology, vol. 9, No. 8, pp. 2067-2078.*
Berg, I. A., et al., 2007, "A 3-hydroxypropionate/4-hydroxybutyrate autotrophic carbon dioxide assimilation pathway in Archaea", Science, vol. 318, pp. 1782-1786.*
Ramey et al., Sep. 17, 2008, "Translation of genomics data into useful metabolic engineering strategies: Construction of a 3-hydroxypropionic acid producing *E. coli*", Abstract/Poster presented by OPX Biotechnologies at the Metabolic Engineering Meeting, Sep. 14-19, Puerto Vallarta, Mexico.*
Lipscomb et al., Sep. 17, 2008, "Understanding production of tolerant 3-hydroxypropionic in a genomic context", Abstract/Poster presented by OPX Biotechnologies at the Metabolic Engineering Meeting, Sep. 14-19, Puerto Vallarta, Mexico.*
Rathnasingh, et al., "Development and Evaluation of Efficient Recombinant *Escherichia coli* Strains for the Production of 3-Hydroxypropionic Acid From Glycerol," Biotechnology and Bioengineering, 2009, pp. 729-739, vol. 104.
Zhu, et al, "Production of 3-hydroxypropionic acid by recombinant *Klebsiella pneumoniae* based on aeration and ORP controlled strategy," Korean Journal Chemical Engineering, 2009, pp. 1679-1685, vol. 26.
Raj, et al, "Effect of process parameters on 3-hydroxypropionic acid production from glycerol using a recombinant *Escherichia coli*," Applied Microbiology Biotechnology, 2009, pp. 649-657, vol. 84.
Raj, et al., "Production of 3-hydroxypropionic acid from glycerol by novel recombinant *Escherichia coli* BL21 strain," Process Biochemistry, 2008, pp. 1440-1446, vol. 43.
Sliniger, et al., "Production of 3-Hydroxypropionaldehyde from Glycerol," Applied and Environmental Microbiology, 1983, pp. 62-67, vol. 46.
Forage, et al., "Glycerol Fermentation in *Klebsiella pnemoniae*: Functions of the Coenzyme B12-Dependent Glycerol and Diol Dehydratases," Journal of Bacteriology, 1982, pp. 413-419, vol. 149.

* cited by examiner

SEQUENCE LISTING

```
<160> NUMBER OF SEQ ID NOS: 10

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
tctagaatga tgaattttca gcacc                                             25

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct

<400> SEQUENCE: 2
ggatccgtta actcaagact ccagggcaat cc                                     32

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
tctagaatga aaagatcaaa acgattt                                           27

<210> SEQ ID NO 4
<211> LENGTH: 24
```

```
<212> TYPE: DNA
<213> ORGANISM: Artificial Sequence
<220> FEATURE:
<223> OTHER INFORMATION: Synthetic Construct

<400> SEQUENCE: 4
ggatccgtca gcggcaatct gcac                                            24

<210> SEQ ID NO 5
<211> LENGTH: 26
<212> TYPE: DNA
<213> ORGANISM: Artificial Sequence
<220> FEATURE:
<223> OTHER INFORMATION: Synthetic Construct

<400> SEQUENCE: 5
aagcttcatg ctctccggcg cctgtc                                          26

<210> SEQ ID NO 6
<211> LENGTH: 28
<212> TYPE: DNA
<213> ORGANISM: Artificial Sequence
<220> FEATURE:
<223> OTHER INFORMATION: Synthetic Construct

<400> SEQUENCE: 6
agatctattt ggtccagcga gctgaagc                                        28

<210> SEQ ID NO 7
<211> LENGTH: 26
<212> TYPE: DNA
<213> ORGANISM: Artificial Sequence
<220> FEATURE:
<223> OTHER INFORMATION: Synthetic Construct

<400> SEQUENCE: 7
agatctcctg ggatttcgcg acggca                                          26

<210> SEQ ID NO 8
<211> LENGTH: 27
<212> TYPE: DNA
<213> ORGANISM: Artificial Sequence
<220> FEATURE:
<223> OTHER INFORMATION: Synthetic Construct

<400> SEQUENCE: 8
aagctttcga caatcggttt taaggtg                                         27

<210> SEQ ID NO 9
<211> LENGTH: 26
<212> TYPE: DNA
<213> ORGANISM: Artificial Sequence
<220> FEATURE:
<223> OTHER INFORMATION: Synthetic Construct

<400> SEQUENCE: 9
gttaacctga cgccgttgga tacacc                                          26

<210> SEQ ID NO 10
<211> LENGTH: 32
<212> TYPE: DNA
<213> ORGANISM: Artificial Sequence
```

```
<220> FEATURE:
<223> OTHER INFORMATION: Synthetic Construct

<400> SEQUENCE: 10
agatctaaaa gcttatgagc tcagccaatc ga                                      32
```

METHOD OF PRODUCING 3-HYDROXYPROPIONIC ACID FROM GLYCEROL

CROSS-REFERENCE TO RELATED APPLICATIONS

This application is filed under the provisions of 35 U.S.C. §371 and claims the priority of International Patent Application No. PCT/KR2009/006278 filed on 29 Oct. 2009 entitled "Novel Method of Producing 3-Hydroxypropionic Acid from Glycerol" in the name of Chul-Ho KIM, et al. which is hereby incorporated by reference herein in its entirety.

TECHNICAL FIELD

The present invention relates to a novel method of producing 3-hydroxypropionic acid from glycerol, and more particularly to a method of producing 3-hydroxypropionic acid by culturing in a glycerol-containing medium a mutant microorganism obtained by amplifying an aldehyde dehydrogenase-encoding gene in a microorganism having the abilities to produce coenzyme B12 and produce 3-hydroxypropionic acid using glycerol as a carbon source.

BACKGROUND ART 3-hydroxypropionic acid which receives attention as a biomass-derived platform chemical together with lactic acid and succinic acid can be used as a raw material for the preparation of 1,3-propanediol, acrylic acid, acrylamide, malonic acid or a biopolymer such as poly-hydroxypropionic acid. Therefore, the development of technology for producing large amounts of 3-hydroxypropionic acid is very important.

Known chemical processes for the production of 3-hydroxypropionic acid include a process of producing 3-hydroxypropionic acid from 1,3-propanediol in the presence of a palladium catalyst (U.S. Pat. No. 5,321,156), a process of producing 3-hydroxypropionic acid from 3-hydroxypropionaldehyde in the presence of a palladium/platinum catalyst (U.S. Pat. No. 5,831,121), a process of producing 3-hydroxypropionic acid using an ion exchange resin (Japanese Patent Publication No. 2000-159724), and a process of producing 3-hydroxypropionic acid from epoxide derivatives in the presence of an acid or base catalyst (Korean Patent No. 10-0408806).

With respect to biological methods, Suthers et al. of the University of Wisconsin reported a method of producing 3-hydroxypropionic acid from glycerol using a recombinant *E. coli* strain that overexpresses a glycerol dehydratase gene derived from *Klebsiella pneumoniae* and an aldehyde dehydrogenase gene derived from *E. coli* or *Saccharomyces cerevisiae* (U.S. Pat. No. 6,852,517). Recently, Rathnasingh et al. reported a novel recombinant *E. coli* strain that produces increased amounts of 3-hydroxypropionic acid from glycerol (Rathnasingh et al., *Biotechnol. Bineng.* 104:729-39. 2009).

However, the method of producing 3-hydroxypropionic acid from glycerol using the recombinant *E. coli* strain has a disadvantage in that the expensive coenzyme adenosylcobalamine (coenzyme B12) is required to be supplied to a culture medium in order to reactivate the glycerol dehydratase enzyme.

Accordingly, the present inventors have made extensive efforts to a method of producing 3-hydroxypropionic acid in large amounts without requiring an expensive additive, and as a result, have found that, when the aldehyde dehydrogenase gene in *Klebsiella pneumoniae* is highly expressed, 3-hydroxypropionic acid can be produced with high productivity without having to add coenzyme 12, thereby completing the present invention.

DISCLOSURE OF INVENTION

It is an object of the present invention to provide a method of producing 3-hydroxypropionic acid with high productivity without requiring an expensive additive.

To achieve the above object, the present invention provides a method for producing 3-hydroxypropionic acid, the method comprising the steps of (a) culturing in a glycerol-containing medium a mutant microorganism obtained by amplifying an aldehyde dehydrogenase-encoding gene in a microorganism having the abilities to produce coenzyme B12 and produce 3-hydroxypropionic acid using glycerol as a carbon source, thereby producing 3-hydroxypropionic acid; and (b) recovering the produced 3-hydroxypropionic acid.

The present invention also provides a method for producing 3-hydroxypropionic acid, the method comprising the steps of culturing in a glycerol-containing medium a mutant microorganism obtained by introducing a 1,3-propanediol oxidoreductase-encoding gene and an aldehyde dehydrogenase-encoding gene into a *Klebsiella pneumoniae* mutant (AK strain) which contains deletions of a glycerol dehydrogenase gene (DhaD), a transcriptional activator gene (DhaR), a 1,3-propanediol oxidoreductase gene (DhaT) and a glycerol dehydratase reactivation factor II gene (DhaBA2), the mutant organism having the ability to produce 3-hydroxypropionic acid using glycerol as a carbon source, thereby producing 3-hydroxypropionic acid; and recovering the produced 3-hydroxypropionic acid.

The present invention also provides a *Klebsiella pneumoniae* mutant obtained by amplifying an aldehyde dehydrogenase-encoding gene in a microorganism having the abilities to produce coenzyme B12 and produce 3-hydroxypropionic acid using glycerol as a carbon source.

BEST MODE FOR CARRYING OUT THE INVENTION

Figure 1:
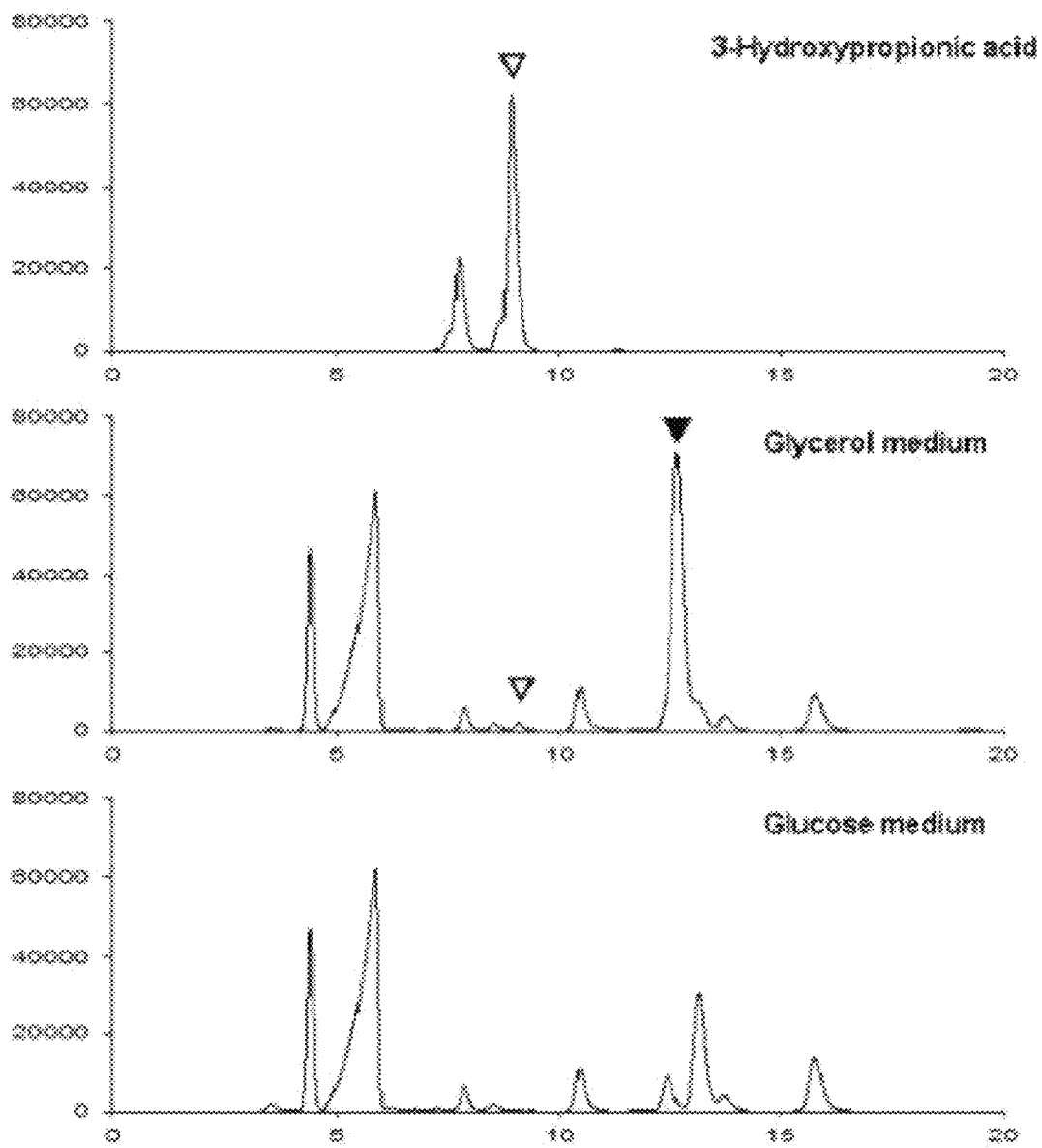
FIG. 1 shows the results of analyzing the metabolic products of a *Klebsiella pneumoniae* Cu strain by liquid chromatography (∇: 3-hydroxypropionic acid; ▼: 1,3-propanediol).

In one aspect, the present invention is directed to a method for producing 3-hydroxypropionic acid, the method comprising the steps of a) culturing in a glycerol-containing medium a mutant microorganism obtained by amplifying an aldehyde dehydrogenase-encoding gene in a microorganism having the abilities to produce coenzyme B12 and produce 3-hydroxypropionic acid using glycerol as a carbon source, thereby producing 3-hydroxypropionic acid; and (b) recovering the produced 3-hydroxypropionic acid.

In the present invention, the microorganism having the abilities to produce coenzyme B12 and produce 3-hydroxypropionic acid using glycerol as the carbon source is a microorganism of the genus *Klebsiella*.

In the present invention, the microorganism having the abilities to produce coenzyme B12 and produce 3-hydroxypropionic acid using glycerol as the carbon source is preferably a microorganism of the genus *Klebsiella*, and most preferably *Klebsiella pneumoniae*.

In one example of the present invention, it was first found that *Klebsiella pneumoniae* produced 3-hydroxypropionic acid from glycerol. In order to increase the ability of the *Klebsiella pneumoniae* strain to produce 3-hydroxypropionic acid, a recombinant strain was constructed by overexpressing an aldehyde dehydratase-encoding gene, which produces 3-hydroxypropionic acid from 3-hydroxypropionaldehyde, in the *Klebsiella pneumoniae* strain by gene recombination, and the recombinant strain was cultured in a glycerol-containing medium. As a result, it was found that the recombinant strain produced 3-hydroxypropionic acid in a yield seven times higher than the wild-type strain.

In the present invention, the medium in step (a) is free of coenzyme B12.

In the present invention, the microorganism having the abilities to produce coenzyme B12 and produce 3-hydroxypropionic acid using glycerol as the carbon source is a microorganism in which the glycerol oxidative pathway was blocked.

The microorganism in which the glycerol oxidative pathway is blocked is a *Klebsiella pneumoniae* AK strain (KCTC 11419BP).

In another aspect, the present invention is directed to a method for producing 3-hydroxypropionic acid, the method comprising the steps of: culturing in a glycerol-containing medium a mutant microorganism obtained by introducing a 1,3-propanediol oxidoreductase-encoding gene and an aldehyde dehydrogenase-encoding gene into a *Klebsiella pneumoniae* mutant (AK strain) which contains deletions of a glycerol dehydrogenase gene (DhaD), a transcriptional activator gene (DhaR), a 1,3-propanediol oxidoreductase gene (DhaT) and a glycerol dehydratase reactivation factor II gene (DhaBA2), the mutant microorganism having the ability to produce 3-hydroxypropionic acid using glycerol as a carbon source, thereby producing 3-hydroxypropionic acid; and recovering the produced 3-hydroxypropionic acid.

In still another aspect, the present invention is directed to a *Klebsiella pneumoniae* mutant obtained by amplifying an aldehyde dehydrogenase-encoding gene in a microorganism having the abilities to produce coenzyme B12 and produce 3-hydroxypropionic acid using glycerol as a carbon source.

In the present invention, a glycerol oxidative pathway in the mutant is blocked.

In the present invention, the mutant is *Klebsiella pneumoniae* AK-VOTHk (KCTC 11569BP).

In the present invention, recovery of 3-hydroxypropionic acid from the culture broth of the mutant can be carried out using conventional isolation techniques including, for example, distillation, electrodialysis, evaporation, chromatography, solvent extraction, and reaction extraction, and these techniques may generally be used in combination to isolate highly pure substances.

As used herein, the expression "amplification" of a gene means additionally introducing a gene present in either the chromosome of an individual or a plasmid so as to be capable of being overexpressed, and the expression "introduction" of a gene means inserting a gene into the chromosome of an individual or transforming a gene into an individual using a recombinant vector.

In the present invention, insertion of the gene into the chromosome of a cell can be carried out using a conventional gene manipulation method known in the art. For example, insertion of the gene can be carried out using a retroviral vector, an adenoviral vector, an adeno-associated viral vector, a herpes simplex viral vector, a poxvirus vector, a lentiviral vector or a non-viral vector.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1

Production of 3-Hydroxypropionic Acid from Glycerol by *Klebsiella pneumoniae* Strain A *Klebsiella pneumoniae* Cu strain (a strain in which the plasmid from a *Klebsiella pneumoniae* MGH78578 strain (ATCC 700721) was cured) obtained by curing the plasmid from the typical glycerol-fermenting microorganism *Klebsiella pneumoniae* was cultured in 50 ml of a medium containing glucose or glycerol as a single carbon source at 37° C. for 30 hours at 120 rpm, and then the production of 3-hydroxypropionic acid was analyzed by chromatography. The medium used in the culture process had the following composition:

A 0.1 M potassium phosphate buffer (pH 7.0) supplemented with 20 g/L glycerol or glucose, and then supplemented 2 g/l $(NH_4)_2SO_4$, 0.2 g/l $MgSO_4$, 0.002 g/l $CaCl_2 2H_2O$, 1 g/l yeast extract, 1 ml iron solution [5 g/l $FeSO_4 7H_2O$, 4 ml HCl (37%, w/v)] and 1 ml trace element solution [70 mg/l $ZnCl_2$, 100 mg/l $MnCl_2 4H_2O$, 60 mg/l $H_3BO_3$, 200 mg/l $CoCl_2 4H_2O$, 20 mg/l $CuCl_2 2H_2O$, 25 mg/l $NiCl_2 6H_2O$, 35 mg/l $Na_2MoO_4 2H_2O$, 4 ml HCl (37%, w/v)]. In addition, 0.5 mM of IPTG and 10 µg/ml of antibiotic tetracycline were added to the medium.

In order to cure the plasmid from *Klebsiella pneumoniae*, *Klebsiella pneumoniae* MGH78578 was cultured several times in an antibiotic-free liquid medium, and then inoculated into a tetracycline-containing or tetracycline-free medium. Then, a colony which did not grow in the tetracycline-containing medium due to loss of the plasmid DNA was selected from the colonies and named "*Klebsiella pneumoniae* MGH78578 Cu". Then, the production of 3-hydroxypropionic acid was analyzed by chromatography.

The chromatography was performed using an Aminex HPX-87H column (Bio-Rad, 300 mm×78 mm) with an Agilent 1200 series refractive index detector (RID). As the mobile phase, 0.5 mM $H_2SO_4$ (flow rate: 0.8 ml/min) was used, and as a standard, commercially available 3-hydroxypropionic acid (Tokyo Chemical Industry Co., LTD) (the first graph in FIG. 1) was used.

As a result, as can be seen in FIG. 1, the *Klebsiella pneumoniae* cultured in the glucose-containing medium did not produce 3-hydroxypropionic acid, whereas it produced 3-hydroxypropionic acid in the glycerol-containing medium (0.2 g/L). In addition, 1,3-propanediol was produced in the glycerol-containing medium.

Figure 2:
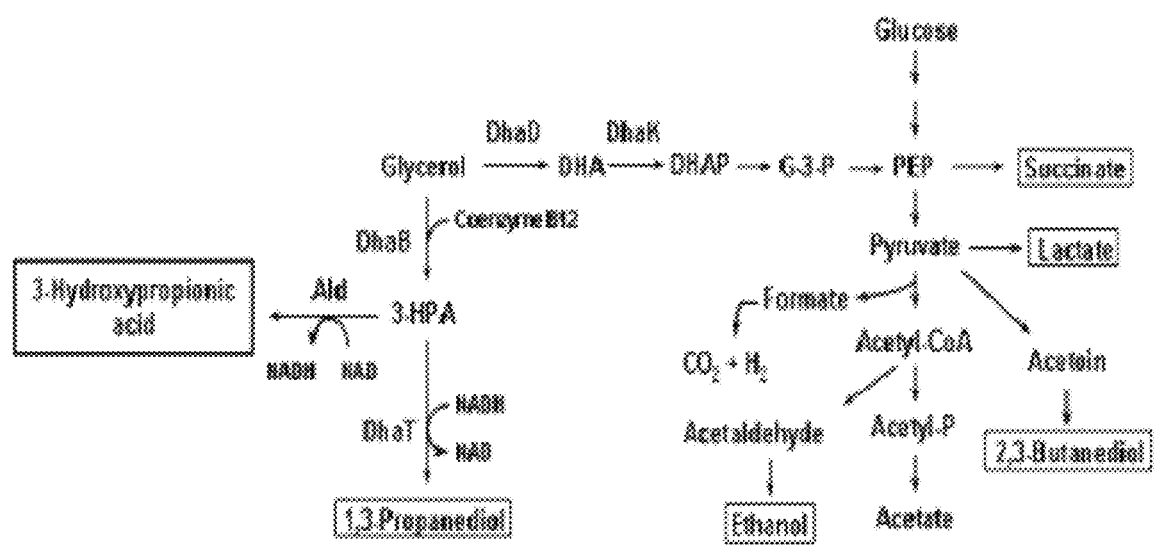
FIG. 2 shows metabolic pathways for the production of 3-hydroxypropionic acid and 1,3-propanediol in *Klebsiella pneumoniae*.

From the above results, a metabolic pathway for the production of 3-hydroxypropionic acid from glycerol in *Klebsiella pneumoniae* as shown in FIG. 2 can be analogized.

Example 2

Development of *Klebsiella pneumoniae* Recombinant Strain Suitable for Production of 3-Hydroxypropionic Acid from Glycerol (1) Construction of Plasmids that Overexpress Aldehyde Dehydrogenase Gene As shown in FIG. 2, aldehyde dehydrogenase was believed to be involved in the production of 3-hydroxypropionic acid from glycerol in the *Klebsiella pneumoniae* strain. Thus, plasmids for overexpressing aldehyde dehydrogenase in *Klebsiella pneumoniae* were constructed.

Specifically, the aldehyde dehydrogenase (AldHk) gene (GenBank database No. ABR76453) was amplified using the chromosomal DNA of the strain as a template with the following primer sequences, and then the amplified DNA was cloned into a pGEM TEasy vector and sequenced. Then, plasmid DNAs were constructed as shown in FIG. 3:

```
SEQ ID NO: 1:
5'-TCTAGAATGATGAATTTTCAGCACC-3'         (AldHk-F)

SEQ ID NO: 2:
5'-GGATCCGTTAACTCAAGACTCCAGGGCAATCC-3'  (AldHk-R)
```

Figure 3:
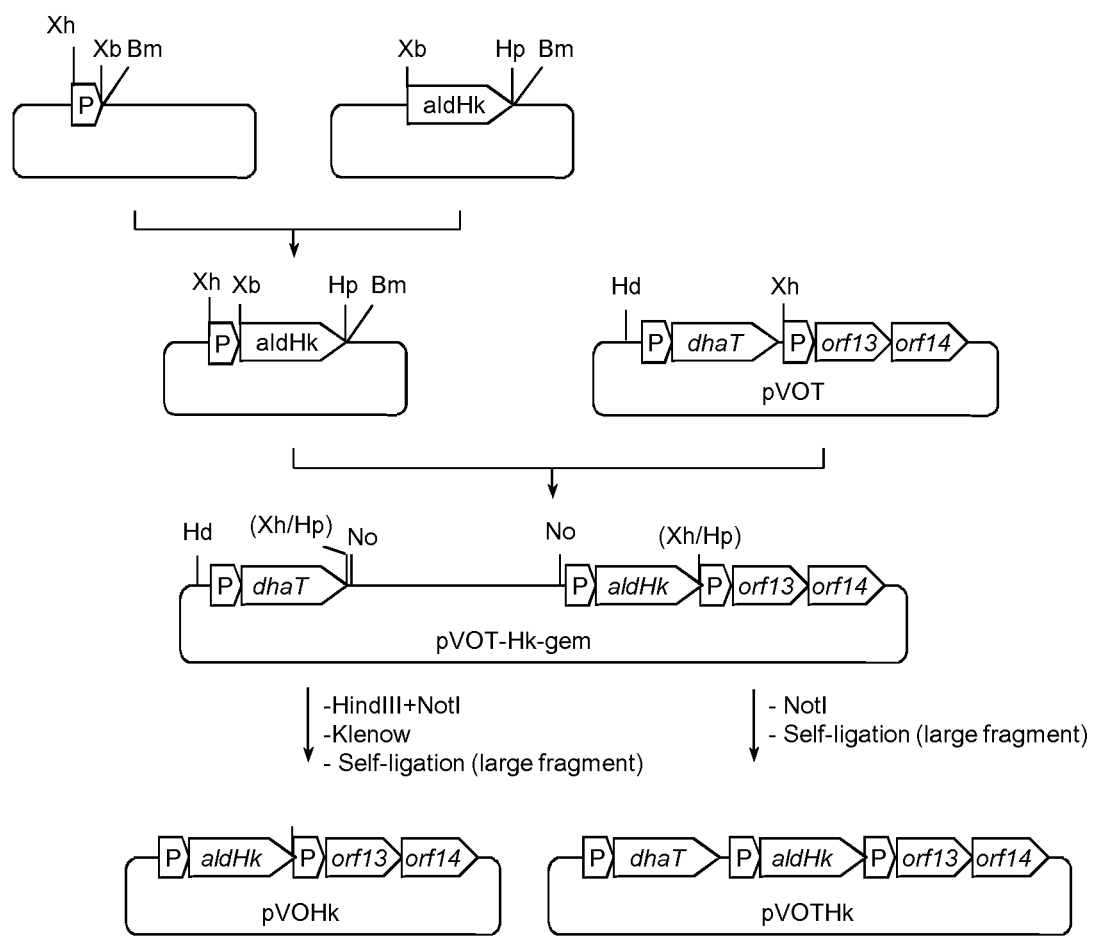
FIG. 3 shows processes for constructing the recombinant plasmids pVOHK and pVOTHk.

As shown in FIG. 3, the aldehyde dehydrogenase AldHk gene of *Klebsiella pneumoniae* was introduced downstream of the lacZ promoter, and then inserted either into a plasmid containing the DhaB reactivation enzyme gene (dhaT) or into a plasmid containing the DhaB reactivation enzyme gene and the 1,3-propanediol oxidoreductase gene (DhaT), thereby constructing the plasmid pVOHk containing the aldehyde dehydrogenase gene and the plasmid pVOTHk containing the aldehyde dehydrogenase gene and the DhaB reactivation enzyme gene.

Figure 4:
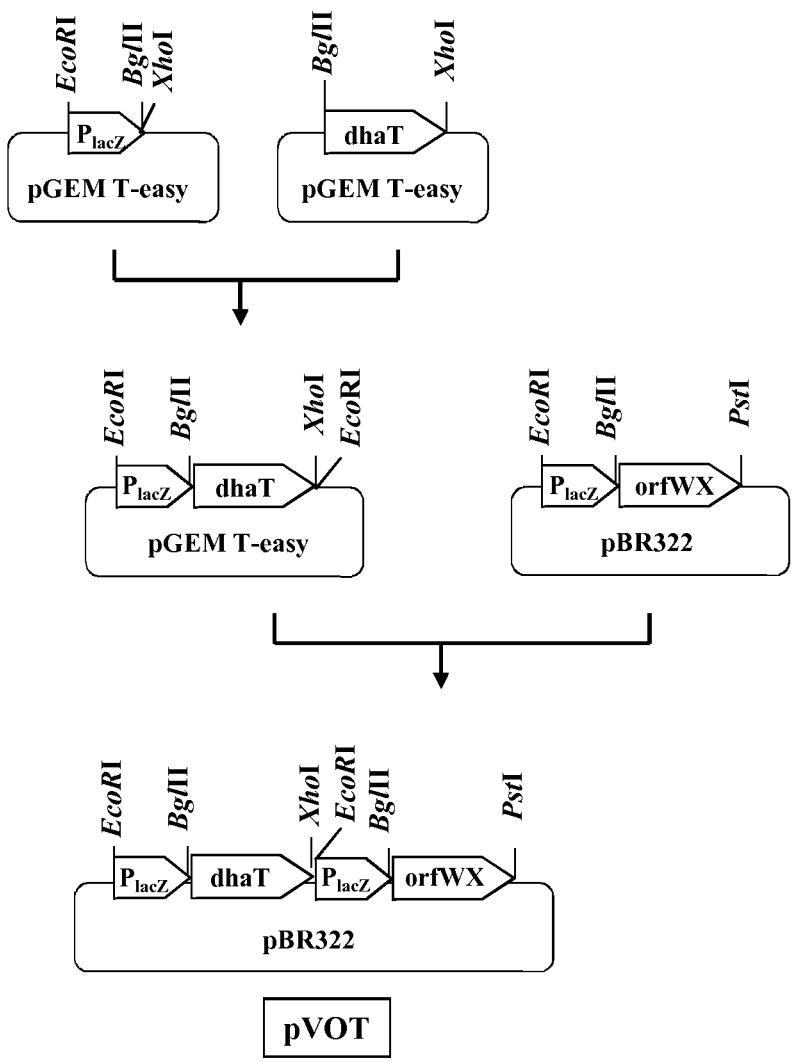
FIG. 4 shows a process for constructing the recombinant plasmid pVOT.

FIG. 4 shows a process for constructing a plasmid (pVO) comprising the DhaB reactivation enzyme gene or a plasmid DNA (pVOT) comprising the DhaB reactivation enzyme gene and the 1,3-propanediol oxidoreductase gene (DhaT). The plasmid pVOT was introduced into *Klebsiella pneumoniae* and named "*Klebsiella pneumoniae* AK-VOT". This recombinant strain was deposited at the Biological Resource Center in the Korea Research Institute of Bioscience and Biotechnology under accession number KCTC 11421BP.

(2) Construction of *Klebsiella pneumoniae* Recombinant Strain in which Glycerol Oxidative-Reductive Pathways were Broken The DhaB enzyme reactivation gene, DhaT gene, DhaR regulator and DhaD gene of the dha regulon (FIG. 5) were substituted with the apramycin-resistant gene by a homologous recombination method using a plasmid DNA-cured *Klebsiella pneumoniae* MGH78578 strain (named "Cu") as a parent strain, thereby preparing a recombinant strain having deletions of both the glycerol oxidative and reductive pathways (hereinafter referred to as the "AK" strain).

DNA fragments for preparing a plasmid for homologous recombination were amplified by PCR using the chromosomal DNA of the *Klebsiella pneumoniae* MGH78578 strain as a template and the following primer sets:

Primer for Amplification of dhaBI Gene Fragments

```
SEQ ID NO: 3:
5'-TCTAGAATGAAAAGATCAAAACGATTT-3'
(dhaBI XbaI-480 bpF)

SEQ ID NO: 4:
5'-GGATCCGTCAGCGGCAATCTGCAC-3'
(dhaBI BamHI-480 bpR)
```

Primer for Amplification of dhaK Gene Fragments

```
SEQ ID NO: 5:
5'-AAGCTTCATGCTCTCCGGCGCCTGTC-3'
(dhaK HindIII-200-700 bpF)

SEQ ID NO: 6:
5'-AGATCTATTTGGTCCAGCGAGCTGAAGC-3'
(dhaK BglII-200-700 bpR)
```

Primer for Amplification of dhaR Gene Fragments

```
SEQ ID NO: 7:
5'-AGATCTCCTGGGATTTCGCGACGGCA-3'
(dhaR bglII-200-700 bpF)

SEQ ID NO: 8:
5'-AAGCTTTCGACAATCGGTTTTAAGGTG-3'
(dhaR HindIII-200-700 bpR)
```

Primer for Amplification of Apr Gene Fragments

```
SEQ ID NO: 9:
5'-GTTAACCTGACGCCGTTGGATACACC-3'
Apr HpaIF

SEQ ID NO: 10:
5'-AGATCTAAAAGCTTATGAGCTCAGCCAATCGA-3'
Apr HindIII-BglIIR
```

The amplified DNA fragments were cloned into a pGEM TEasy vector and sequenced. Then, as shown in FIG. 5, a plasmid DNA was constructed using the vector.

Figure 5:
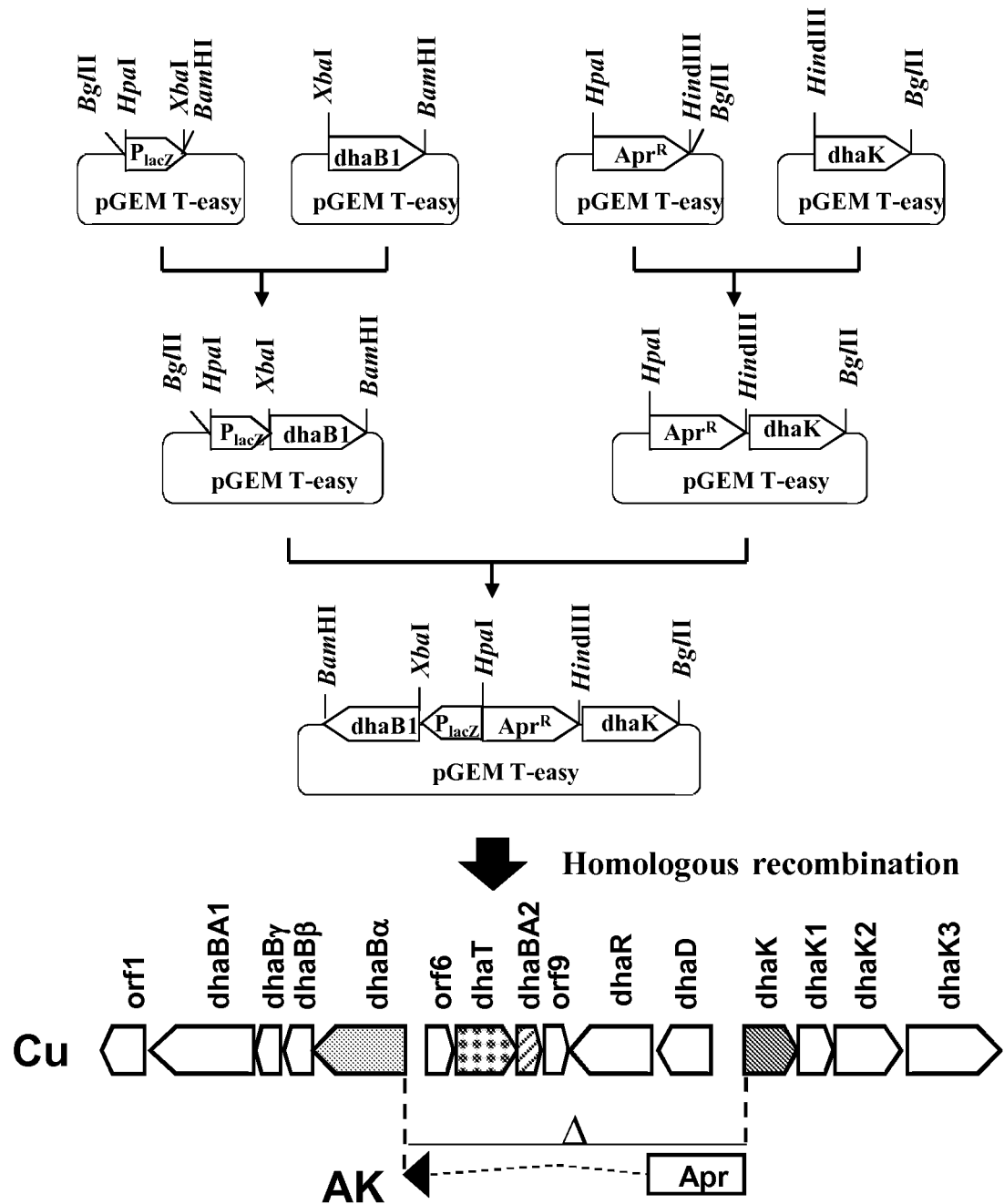
FIG. 5 shows a process for constructing a *Klebsiella pneumoniae* AK mutant strain.

In the method shown in FIG. 5, the plasmid DNA for preparing the AK strain comprising a linkage of DhaB gene amino terminus (dhaB')-LacZ promoter ($P_{lacZ}$)-apramycin resistant gene-DhaK gene amino terminus (dhaK') was constructed.

The plasmid was treated with BamHI-BglII, and the collected DNA fragment was introduced into the *Klebsiella pneumoniae* Cu strain by electroporation. Then, recombinant strains that formed colonies in a medium supplemented with apramycin were isolated from the Cu strain cells. As a result, a recombinant *Klebsiella pneumoniae* AK strain (KCTC 11419BP) with deletions of the DhaB enzyme reactivation gene, DhaT gene, DhaR regulator and DhaD gene of the dha regulon and insertions of the lacZ promoter and the apramycin resistant gene was obtained.

(3) Overexpression of Aldehyde Dehydrogenase Gene in Mutant Strain in which Anaerobic Metabolic Pathway of Glycerol was Blocked Each of the plasmid pVOHk containing the aldehyde dehydrogenase gene and the plasma pVOTHk containing the aldehyde dehydrogenase gene and the DhaB reactivation enzyme gene was introduced by electroporation into each of the *Klebsiella pneumoniae* Cu and AK strains. As a control, a plasmid DNA containing the DhaB reactivation enzyme gene or a plasmid DNA containing the DhaB reactivation enzyme gene and the 1,3-propanediol oxidoreductase gene was used. The recombinant strain AK-VOTHk constructed in this Example was deposited on Oct. 7, 2009 at the Korean Collection for Type Cultures in the Korea Research Institute of Bioscience and Biotechnology under accession number KCTC 11569BP, in accordance with the Budapest Treaty.

TABLE 1

Recombinant strains and plasmid DNAs used or constructed in the present invention Strains

| | |
|---|---|
| E. coli DH5a | Cloning Host |
| K. pneumoniae Cu | TetR contained Plasmid DNA curing K. pneumoniae MGH 78578 |
| K. pneumoniae AK | (orfY-dhaT-orfW-orfX-dhaR-dhaD)::PLacZ-AprR |

Plasmids

| | |
|---|---|
| pV | pBR322 |
| pVO | pBR322-PLacZorfW-orfX |
| pVOT | pBR322-PLacZorfW-orfX-PLacZdhaT |
| pVOHk | pBR322-PLacZorfW-orfX-PLacZaldHk |
| pVOTHk | pBR322-PLacZorfW-orfX-PLacZaldHk-PLacZdhaT |

Each of the recombinant strains prepared in Example 2 was cultured under the same medium conditions (carbon source: glycerol) as Example 1 at 37° C. at 120 rpm, while metabolic products in the culture broth analyzed under the same conditions as Example 1.

Figure 6:
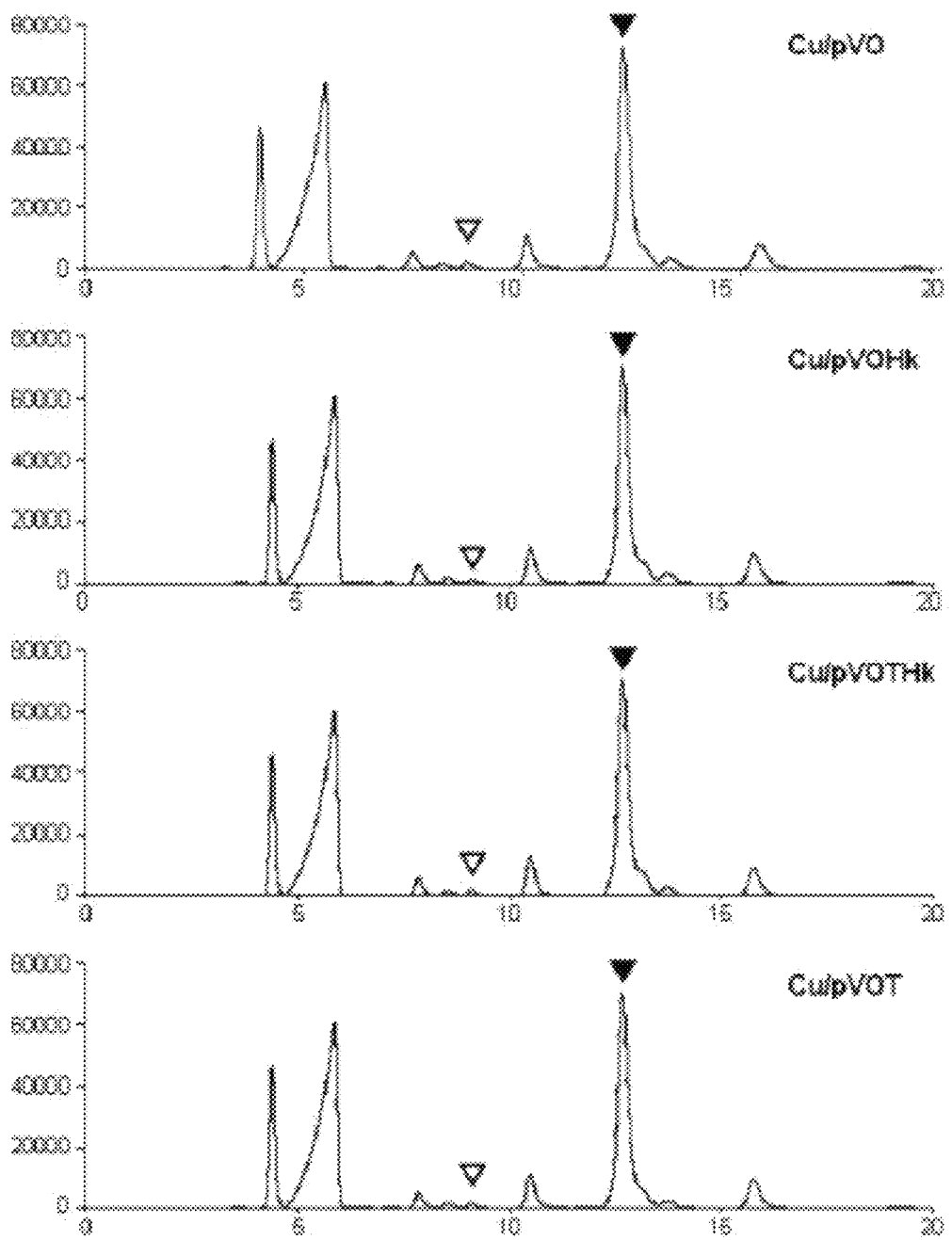
FIG. 6 shows the results of analyzing the metabolic products of a *Klebsiella pneumoniae* Cu-derived recombinant strain by liquid chromatography (∇: 3-hydroxypropionic acid; ▼: 1,3-propanediol).
Figure 7:
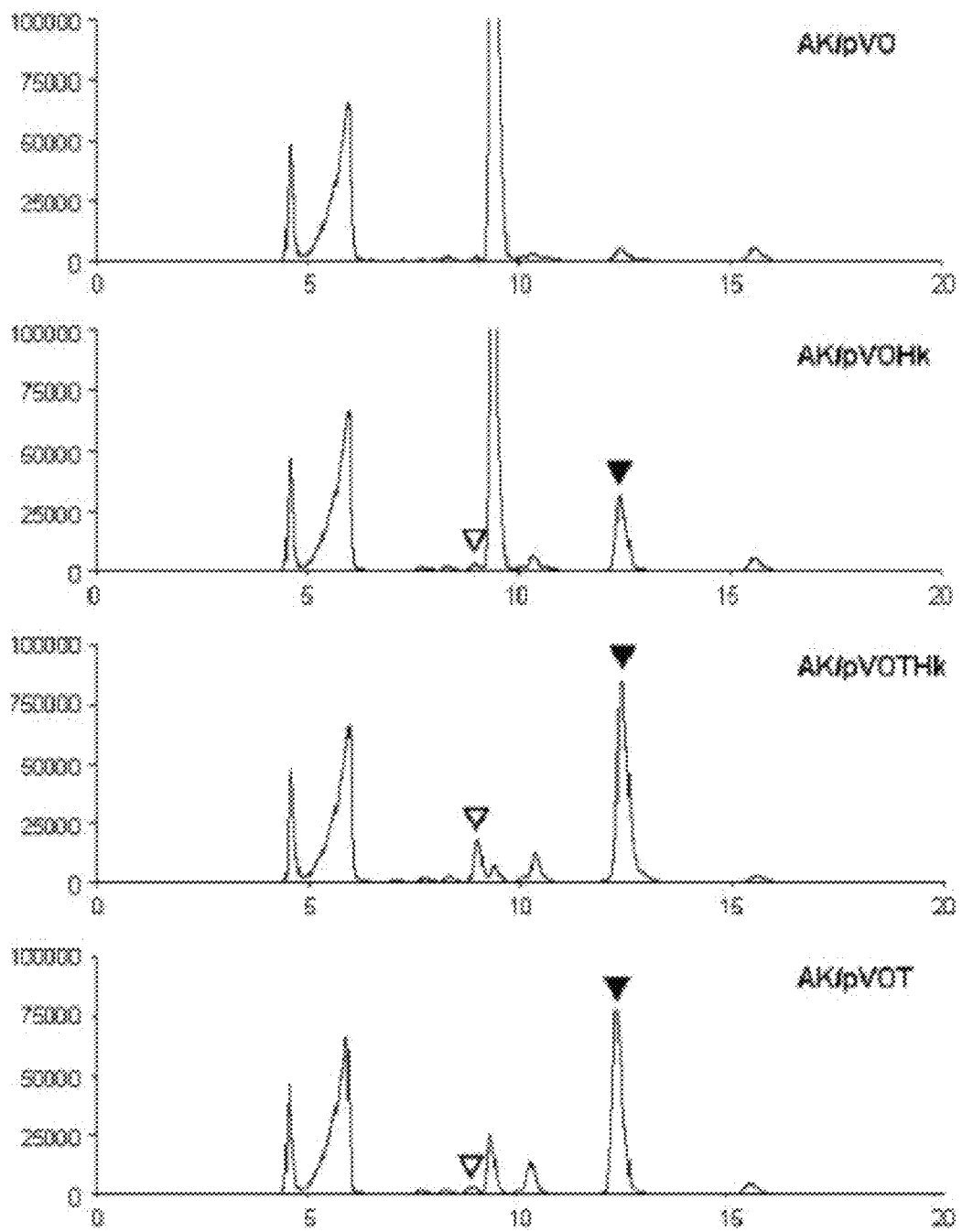
FIG. 7 shows the results of analyzing the metabolic products of a *Klebsiella pneumoniae* AK-derived recombinant strain by liquid chromatography (∇: 3-hydroxypropionic acid; ▼: 1,3-propanediol).

As a result, it was shown that the *Klebsiella pneumoniae* Cu-derived recombinant strains cultured for 20 hours produced 1,3-propanediol and 3-hydroxypropionic acid while completely consuming the glycerol added, but the production of 3-hydroxypropionic acid was not substantially influenced by the high expression of the aldehyde dehydrogenase alkHk gene (FIG. 6 and Table 2). Meanwhile, it was observed that the production of 3-hydroxypropionic acid in which the mutant strain AK-derived recombinant strain in which the glycerol oxidative pathway had been blocked significantly increased (FIG. 7). The production of 3-hydroxypropionic acid in the AK-pVOTHk strain was at least 7 times higher than that in the CU strain (Table 3).

TABLE 2

Contents of metabolic products produced by flask culture of *Klebsiella pneumoniae* Cu-derived recombinant strains

| Metabolic products (g/L) | Cu/pVO | Cu/pVOHk | Cu/pVOTHk | Cu/pVOT |
|---|---|---|---|---|
| remaining glycerol | 0 | 0 | 0 | 0 |
| 1,3-propanediol | 7.96 | 7.80 | 7.85 | 7.67 |
| 3-hydroxypropionic acid | 0.28 | 0.16 | 0.29 | 0.21 |
| 2,3-Butandiol | 1.34 | 1.19 | 1.28 | 1.20 |
| Ethanol | 0.14 | 0.50 | 0.23 | 0.43 |
| Lactic acid | 0.17 | 0.18 | 0.17 | 0.17 |
| Succinic acid | 0.55 | 0.58 | 0.56 | 0.54 |
| Acetic acid | 1.68 | 1.77 | 1.97 | 1.77 |

TABLE 3

Contents of metabolic products produced by flask culture of *Klebsiella pneumoniae* AK-derived recombinant strains

| Metabolic products (g/L) | AK/pVO | AK/pVOHk | AK/pVOTHk | AK/pVOT |
|---|---|---|---|---|
| remaining glycerol | 14.85 | 8.65 | 0.15 | 1.48 |
| 1,3-propanediol | 0.51 | 3.44 | 9.65 | 8.43 |
| 3-hydroxypropionic acid | 0.25 | 0.52 | 2.07 | 0.57 |
| 2,3-Butandiol | 0 | 0 | 0 | 0 |
| Ethanol | 0 | 0 | 0 | 0 |
| Lactic acid | 0.23 | 0.24 | 0.25 | 0.25 |
| Succinic acid | 0.14 | 0.26 | 0.25 | 0.29 |
| Acetic acid | 0.55 | 1.37 | 2.06 | 2.21 |

Example 3

Production of 3-hydroxypropionic Acid from Glycerol by Culture of *Klebsiella pneumoniae* AK-VOTHk Strain The *Klebsiella pneumoniae* AK-VOTHk strain was cultured in a 5-L fermentor, and the degree of growth of the strain was examined. In addition, the amount of glycerol remaining in the culture supernatant and the production of metabolic products, including 3-hydroxypropionic acid and 1,3-propanediol, were analyzed by chromatography.

The medium used in the culture process had the following composition:
20 g/l glycerol, 3.4 g/l $K_2HPO_4$, 1.3 g/l $KH_2PO_4$, 0.2 g/l $MgSO_4$, 0.002 g/l $CaCl_2 2H_2O$, 1 g/l yeast extract, 1 ml iron solution [5 g/l $FeSO_4 7H_2O$, 4 ml HCl (37%, w/v)] and 1 ml trace element solution [70 mg/l $ZnCl_2$, 100 mg/l $MnCl_2 4H_2O$, 60 mg/l $H_3BO_3$, 200 mg/l $CoCl_2 4H_2O$, 20 mg/l $CuCl_2 2H_2O$, 25 mg/l $NiCl_2 6H_2O$, 35 mg/l $Na_2MoO_4 2H_2O$, 4 ml HCl (37%, w/v)].

TABLE 4

Contents of metabolic products produced by *Klebsiella pneumoniae* AK-VOTHk recombinant strain in 5-L fermentor

| Metabolic products (g/L) | 3 h | 6 h | 9 h | 12 h | 15 h | 18 h | 21 h | 24 h | 30 h | 39 h | 45 h |
|---|---|---|---|---|---|---|---|---|---|---|---|
| Remaining glycerol | 19.8 | 17.2 | 13.0 | 9.2 | 6.4 | 1.5 | 0 | 0 | 0 | 0 | 0 |
| 1,3-propanediol | 0 | 2.0 | 3.8 | 5.8 | 7.0 | 9.2 | 8.9 | 8.7 | 8.3 | 8.1 | 8.1 |
| 3-hydroxypropionic acid | 0 | 0.5 | 1.0 | 1.7 | 2.4 | 3.9 | 4.5 | 5.5 | 5.8 | 5.9 | 6.0 |
| 2,3-Butandiol | 0 | 0 | 0 | 0 | 0 | 0 | 0 | 0 | 0 | 0 | 0 |
| Ethanol | 0 | 0 | 0 | 0 | 0 | 0 | 0 | 0 | 0 | 0 | 0 |
| Lactic acid | 0 | 0 | 0 | 0 | 0.1 | 0.2 | 0.2 | 0.2 | 0.2 | 0.2 | 0.3 |

TABLE 4-continued

Contents of metabolic products produced by *Klebsiella pneumoniae* AK-VOTHk recombinant strain in 5-L fermentor

| Metabolic products (g/L) | 3 h | 6 h | 9 h | 12 h | 15 h | 18 h | 21 h | 24 h | 30 h | 39 h | 45 h |
|---|---|---|---|---|---|---|---|---|---|---|---|
| Succinic acid | 0 | 0 | 0 | 0 | 0 | 0 | 0 | 0 | 0 | 0 | 0 |
| Acetic acid | 0 | 1.7 | 1.2 | 1.9 | 2.8 | 3.3 | 3.5 | 3.6 | 3.8 | 4.2 | 4.1 |
| 3-HP/glycerol (mol/mol) | 0 | 0.18 | 0.15 | 0.16 | 0.18 | 0.21 | 0.25 | 0.30 | 0.32 | 0.33 | 0.33 |
| 3-HP productivity (g/Lh) | 0. | 0.08 | 0.11 | 0.14 | 0.16 | 0.21 | 0.21 | 0.23 | 0.19 | 0.15 | 0.13 |

The culture process was carried out under the following conditions: the effective volume of the 5 L fermentor: 2 L, the final concentration of IPTG: 0.5 mM, the final concentration of tetracycline: 10 μg/L, inoculation concentration: 1%, culture temperature: 37° C., stirring rate: 200 rpm, and aeration rate: 0.5 vvm.

Figure 8:
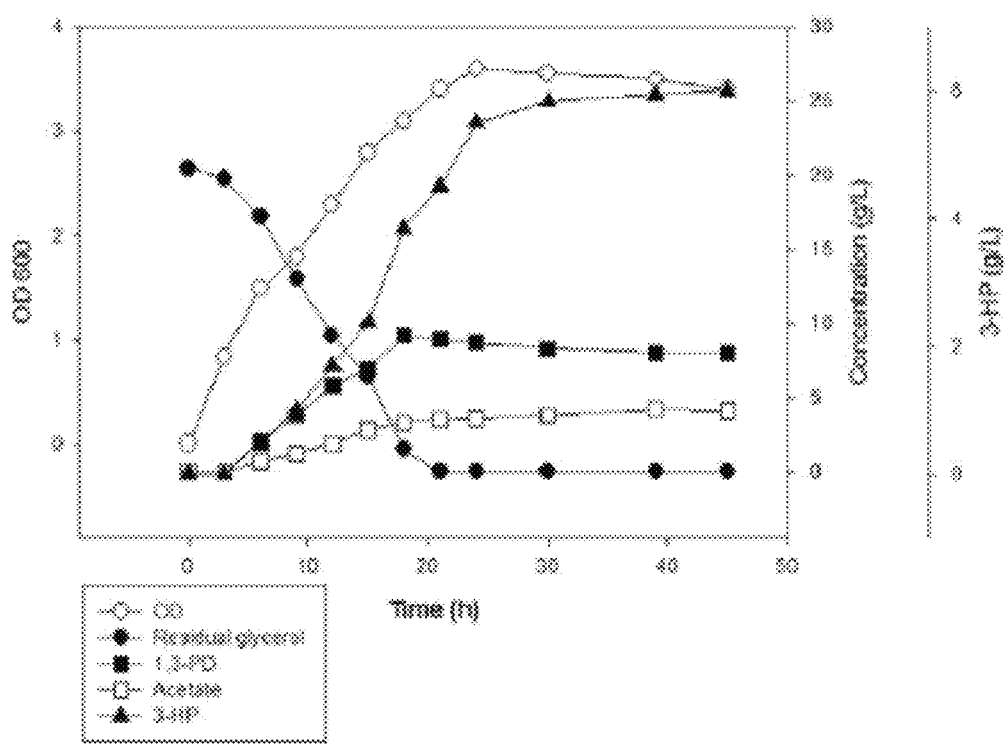
FIG. 8 shows the results of culture of a *Klebsiella pneumoniae* AK-VOTHk strain in a 5-L fermentor.

As a result, as shown in FIG. 8, the strain completely consumed glycerol at 21 hours of culture, in which the production, conversion rate and productivity of 3-hydropropionic acid were 4.5 g/L, 0.25 (mol/mol) and 0.21 g/Lh, respectively. Even after glycerol added was completely consumed, the production of 3-hydroxypropionic acid slowly increased to a level of 6.0 g/L, and this increase appeared to be attributable to the conversion of the produced 1,3-propanediol to 3-hydroxypropionic acid.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The present invention enables the fermentation of glycerol even under microaerobic or aerobic conditions without having to add coenzyme B12. Thus, it is expected that the invention will be very suitable for the development of biological processes for producing large amounts of 3-hydroxypropionic acid.

What is claimed is:

1. A method for producing 3-hydroxypropionic acid by culturing *Klebsiella pneumoniae* AK-VOTHk (KCTC 11569BP) having the ability to produce coenzyme B12 and 3-hydroxypropionic acid using glycerol as a carbon source that has a deletion of the chromosomal glycerol dehydrogenase gene (DhaD), transcriptional activator gene (DhaR), 1,3-propanediol oxidoreductase gene (DhaT) and glycerol dehydratase reactivation factor II gene (DhaBA2) and is transformed with a plasmid comprising a 1,3-propanediol oxidoreductase-encoding gene, an aldehyde dehydrogenase-encoding gene, and a glycerol dehydratase gene (DhaB1), each under the control of an inducible promoter, the method comprising the steps of:

(a) culturing *Klebsiella pneumoniae* AK-VOTHk (KCTC 11569BP) in a glycerol-containing medium free of coenzyme B12, thereby producing 3-hydroxypropionic acid; and (b) recovering the produced 3-hydroxypropionic acid.

2. A *Klebsiella pneumoniae* mutant, *Klebsiella pneumoniae* AK-VOTHk (KCTC 11569BP), having the ability to produce coenzyme B12 and 3-hydroxypropionic acid using glycerol as a carbon source that has a deletion of the chromosomal glycerol dehydrogenase gene (DhaD), transcriptional activator gene (DhaR), 1,3-propanediol oxidoreductase gene (DhaT) and glycerol dehydratase reactivation factor II gene (DhaBA2) and is transformed with a plasmid comprising a 1,3-propanediol oxidoreductase-encoding gene, an aldehyde dehydrogenase-encoding gene, and a glycerol dehydratase gene (DhaB1), each under the control of an inducible promoter.

* * * * *